United States Patent [19]

Fanta et al.

[11] 4,194,998

[45] Mar. 25, 1980

[54] HIGHLY ABSORBENT POLYHYDROXY POLYMER GRAFT COPOLYMERS WITHOUT SAPONIFICATION

[75] Inventors: George F. Fanta, Peoria, Ill.; Edward I. Stout, Waco, Tex.; William M. Doane, Morton, Ill.

[73] Assignee: The United States of America as represented by the Secretary of Agriculture, Washington, D.C.

[21] Appl. No.: 955,828

[22] Filed: Oct. 30, 1978

Related U.S. Application Data

[63] Continuation-in-part of Ser. No. 748,032, Dec. 6, 1976, Pat. No. 4,134,863.

[51] Int. Cl.$^2$ .............................................. C08L 3/02
[52] U.S. Cl. ..................... 260/17.4 GC; 47/DIG. 10; 106/213; 128/284; 128/285; 128/296; 210/24; 252/316; 435/178
[58] Field of Search ............................... 260/17.4 GC

[56] References Cited

U.S. PATENT DOCUMENTS

| | | | |
|---|---|---|---|
| 3,770,673 | 11/1973 | Slagel et al. | 260/17.4 GC |
| 3,826,767 | 7/1974 | Hoover et al. | 260/17.4 GC |
| 3,889,678 | 6/1975 | Chatterjee et al. | 260/17.4 GC |
| 4,028,290 | 6/1977 | Reid | 260/17.4 GC |
| 4,076,663 | 2/1978 | Masuda et al. | 260/17.4 GC |
| 4,134,863 | 1/1979 | Fanta et al. | 260/17.4 GC |

*Primary Examiner*—Edward M. Woodberry
*Attorney, Agent, or Firm*—M. Howard Silverstein; David G. McConnell; Curtis P. Ribando

[57] ABSTRACT

Absorbent compositions comprising graft copolymers of starch are prepared by a simplified method of synthesis. By using a mixture of a nonionic acrylic monomer and an anionic sulfonic acid-substituted acrylic monomer, highly absorbent compositions are prepared without the need for an alkaline saponification step. These compositions are also characterized by their ability to absorb large amounts of aqueous fluids under highly acidic conditions.

16 Claims, No Drawings

HIGHLY ABSORBENT POLYHYDROXY POLYMER GRAFT COPOLYMERS WITHOUT SAPONIFICATION

CROSS-REFERENCE TO RELATED APPLICATION

This application is a continuation-in-part of copending application Ser. No. 748,032, filed on Dec. 6, 1976, now U.S. Pat. No. 4,134,863 issued Jan. 16, 1979.

BACKGROUND OF THE INVENTION

1. Field of the Invention

Our invention relates to the preparation of graft copolymer compositions which absorb up to about 2,000 times their weight of deionized water and proportionately large quantities of other aqueous fluids.

2. Description of the Prior Art

Polymeric substances which possess the ability to absorb aqueous fluids are known in the prior art. For example, U.S. Pat. Nos. 3,669,103 and 3,810,468 disclose that a variety of monomers may be polymerized, with crosslinking, to give polymeric absorbents. The crosslinking reaction is of critical importance, since the noncrosslinked polymers are water soluble and thus have no utility as absorbents.

Water-absorbing alkali metal salts of saponified granular starch-PAN graft copolymers are disclosed in U.S. Pat. No. 3,661,815. In this disclosure, starch is graft polymerized in the granule state, and the saponification is carried out in an alcohol-containing medium to obtain a granular insoluble absorbent. U.S. Pat. No. 3,932,322 discloses a mixture of the composition of U.S. Pat. No. 3,661,815 with fumed silica or alumina. This mixture exhibits an increased rate of fluid uptake and a decreased tendency toward dusting.

Water-absorbing alkali metal salts of saponified gelatinized starch-PAN graft copolymers are disclosed in U.S. Pat. No. 3,935,099, herein incorporated by reference. In this disclosure, starch is gelatinized by heating in water prior to graft polymerization; also, the graft copolymer is saponified in water to give a viscous dispersion of highly swollen but still insoluble microgel particles. Contrary to the absorbent composition of U.S. Pat. No. 3,661,815, the composition of U.S. Pat. No. 3,935,099 may be dried to a continuous film which has an unusually high absorbency for aqueous fluids. Moreover, this film-forming tendency permits a variety of substrates to be coated with thin films of the absorbent composition and thus leads to dramatic increases in fluid absorbencies of the substrates.

U.S. Pat. No. 4,045,387 discloses highly absorbent polymeric compositions prepared by essentially the same process disclosed in U.S. Pat. No. 3,935,099 except that flour is substituted for the starch. These flour-derived absorbents have higher water absorbencies than the corresponding products derived from starch. However, like the starch-derived products of U.S. Pat. No. 3,935,099, these compositions require saponification of the graft copolymer to convert the hydrophobic synthetic polymer moiety to a hydrophilic entity which is capable of absorbing aqueous fluids. This step is time consuming and involves the use of a considerable amount of energy as heat in order to drive it to completion. Moreover, these prior art compositions become substantially nonabsorbent at pH's less than about 4.

SUMMARY OF THE INVENTION

We have now unexpectedly discovered that in the preparation of highly absorbent compositions comprising graft copolymers, the alkaline saponification step previously required can be eliminated, and that unsaponified compositions can be obtained which will absorb large amounts of aqueous fluids under highly acidic conditions. These surprising results are obtained by a method of preparation comprising the following steps:

a. graft polymerizing a nonionic acrylic monomer and an anionic sulfonic acid-substituted acrylic monomer onto a starch substrate, thereby forming a water-insoluble graft copolymer, wherein the copolymerized nonionic monomer and anionic monomer comprise a synthetic copolymer moiety of the graft copolymer, and the weight ratio of nonionic monomer:anionic monomer in the synthetic copolymer moiety is in the range of about 9:1 to about 1:4, and wherein the weight ratio of starch:synthetic copolymer moiety is in the range of 3:1 to 1:3;

b. drying the water-insoluble graft copolymer from step (a) to a moisture level in the range of about 1 to 15% water by dry weight; and c. recovering the graft copolymer from step (b).

DETAILED DESCRIPTION OF THE INVENTION

As a starting material in the instant invention, it is preferred to use substantially pure unmodified starch. Suitable sources for the starch include both cereal grains and root crops such as corn, wheat, rice, potato, and tapioca. Starch-containing materials could be substituted for the pure starch, exemplary of which are yellow corn flour, bleached corn flour, soft wheat flour, and whole ground corn meal. The amylose and amylopectin components of starch as well as modified starch products such as partially depolymerized starches and derivatized starches may also be used. The term "starch" will be generically used in the ensuing disclosure to include all of the above-mentioned materials and substantial equivalents thereof.

It is well known that unmodified starch in the granule state is insoluble in water at ambient temperatures. It is also known that when a water suspension of unmodified granular starch is heated, the starch granules reversibly take up water with limited swelling, and then, at a definite temperature, typically about 70° C., the granules undergo irreversibly a sudden rapid swelling. As the temperature is increased beyond about 70° C., the granules become more swollen and disrupted, and a higher percentage of starch is solubilized until, at a temperature of about 80°–100° C., a smooth, viscous dispersion is obtained. Starch or starch-containing materials in this form will be referred to as gelatinized. Although gelatinized starch generally affords products of higher absorbency, either granular or gelatinized starch may be used to prepare the products of the instant invention.

The nonionic component which contributes to the synthetic copolymer moiety may be an acrylic monomer that yields either (1) water-soluble or (2) water-insoluble polymers when allowed to polymerize under free radical conditions. Acrylamide is the preferred water-soluble variety since the relatively strong hydrophilic nature of polyacrylamide imparts a high affinity for water to the final graft copolymer. Acrylonitrile is the preferred water-insoluble type, though it is understood that other hydrophobic comonomers such as methyl acrylate and methyl methacrylate could be substituted as substantial equivalents thereof.

The anionic component contributing to the synthetic copolymer moiety is selected from the class of sulfonic acid-substituted acrylic comonomers as known in the art. A preferred monomer in this group is 2-acrylamido-2-methylpropane sulfonic acid ($AASO_3H$). An example of another anionic monomer, without limitation thereto, is 2-sulfoethyl methacrylate (2-SEM). Also, it is understood that metal salts of these acids, e.g., sodium or potassium, may be substituted for the free acids themselves.

The preferred proportions of the above-mentioned nonionic and anionic monomers with respect to one another and with respect to the starch substrate are dependent upon a number of factors including the species of monomers selected, the type and state of the starch, and the conditions of graft initiation. Generally, the weight ratio of nonionic monomer:anionic monomer must be in the range of about 9:1 to about 1:4 which corresponds to the range of proportions required in the synthetic copolymer moiety of the graft copolymer in order to impart absorbency. The preferred weight ratio of starch to the synthetic copolymer moiety is in the range of about 1:1 to about 2:3, though it may range as high as 3:1 and as low as 1:3. These values correspond to a 40–60% add-on for the preferred range and a 25–75% add-on for the outside range, wherein the percent add-on is the weight percent synthetic polymer in the starch graft copolymer. For a particular combination of nonionic and anionic monomers, starch type, and reaction conditions, the optimum proportions within the above-described ranges could be readily determined by measurement of the aqueous fluid absorbency of the resultant product. For example, the absorbencies observed for an acrylonitrile-$AASO_3H$ system indicate that when the starch:synthetic moiety is in a ratio of 1:2, then the AN:$AASO_3H$ ratio should be in the range of about 1:1 to about 3:5 (see Table III, below).

Starch graft copolymers are well known in the prior art, and various methods and procedures used to synthesize these graft copolymers from a variety of monomer systems have been reviewed by Fanta, *Block and Graft Copolymerization*, R. J. Ceresa, ed., John Wiley & Sons, 1973, Chapter 1. In Fanta's review, the influence of such variables as type of initiator used, type of pretreatment of starch, kinds of polymerization media employed, amounts of monomer used, and the like on starch graft copolymer compositions are considered. Any of the conventional initiating systems, such as those described by Fanta could be applied to the instant invention. The preferred graft polymerization initiators are ceric ammonium nitrate, the ferrous sulfate-hydrogen peroxide redox system, and Cobalt-60 irradiation. Others would include, for example, ozone, Mn (III), and electron beam irradiation.

Although most of the absorbent compositions cited in the following examples are isolated by alcohol precipitation, it is obvious that any of the isolation methods known in the prior art including those in U.S. Pat. No. 3,935,099 may be used. These methods include drum drying, freeze drying, spray drying, flash drying, and dialysis followed by tray drying. The dried starch graft copolymer has a moisture content preferably in the range of about 1 to 15% by weight. When the starch used as the starting material is granular, it is sometimes necessary for obtaining high absorbencies to disperse the graft copolymer by briefly heating in water and then drying the resulting aqueous dispersion. It may also be desirable to titrate the aqueous graft copolymer dispersion with alkali to near neutrality prior to heating in order to avoid any acid-catalyzed hydrolysis of the polysaccharide moiety.

The resulting unsaponified starch graft copolymer absorbents are highly acidic in nature having a pH of about 2–3, and they are characterized by the ability to absorb aqueous fluids at pH's less than 4. For example, when 0.1 g. of the graft copolymer of Example 12, infra, was added to 20 ml. of distilled water, the pH of the resulting gel was 2.8. This graft copolymer absorbed 230 times its weight of water which had been acidified to pH 3.2 (see Example 13). At these low pH values, starch graft copolymer absorbents known in the prior art would precipitate from aqueous dispersion and would thus be of limited utility. The instant compositions will also absorb from about 100 to about 2,000 times their weight of distilled water at neutral pH, and from about 12–30 times their weight of synthetic urine.

Since the prior art discloses the use of graft copolymer absorbents for: (1) the reduction of the water content of emulsions, suspensions, and dispersions; (2) the coating of various substrates to increase their water-holding capacity; (3) the solidification of sewage sludge and other waste materials to facilitate handling and drying; and (4) the entrapment and immobilization of enzymes, it is obvious that the instant absorbent polymers would also function for these applications.

Another application for these absorbent polymers is for thickening aqueous systems. Although films or particles of these absorbent compositions retain their integrity as they swell and imbibe water, it is obvious that a film or particle which has imbibed several hundred times or 1,000 times its weight of water will not possess a large degree of mechanical strength and can therefore be broken up with a minimum of effort to give a smooth, viscous dispersion. The products of the instant invention are thus particularly well suited for use as thickeners. Moreover, since the absorbent polymer compositions swell rapidly but do not actually dissolve, they do not show the undesirable tendency to form surfacehydrated lumps or "gumballs", which is so prevalent in prior art thickeners. There are also numerous other applications for these absorbents, which are not specifically listed but which will be readily apparent to those skilled in the art.

The following examples are intended only to further illustrate the invention and are not intended to limit the scope of the invention which is defined by the claims.

EXAMPLES 1–4

A solution of $AASO_3H$ and acrylamide (10 g. total) in 10 ml. of water was prepared in a 2-oz. screw cap bottle. Pregelatinized wheat starch (10 g., dry basis; water content, 10.6%) was added and the mixture blended with a spatula to give a heavy dough. Oxygen was removed from the mixture by evacuating to 50 mm. and repressuring with nitrogen a total of four times. The bottle was capped, irradiated with Cobalt-60 to a total dose of 0.5 Mrad, and then let stand at ambient temperature for 2 hours. The reaction mass was cut into small pieces, and blended under high shear with isopropanol to give the graft copolymer as a granular product. The graft copolymer was removed by filtration, exhaustively extracted with isopropanol to remove any unreacted monomer, and allowed to air dry. The graft copolymer (moisture content of 4–14%) was finally ground to pass a 60-mesh sieve.

Weight percent synthetic polymer in the graft copolymer (% add-on) was calculated from the gain in weight of starch due to graft polymerization, after correcting for the moisture content of the sample.

To determine water absorbency, an accurately weighed 1–10 mg. sample of graft copolymer (amount used depended on absorbency) was added to 50 ml. of distilled water and allowed to stand for 30 minutes. Water was then separated from swollen gel particles by screening through a tared 280-mesh sieve which was 4.8 cm. in diameter. The sieve was allowed to drain for 20 minutes and was then weighed to determine the amount of water-swollen gel. Water absorbency was then calculated as grams of water per gram of dry graft copolymer. To determine synthetic urine absorbency, the above procedure was repeated using about 50 mg. of absorbent polymer in a solution composed of 97.07% distilled water, 1.94% urea, 0.80% NaCl, 0.11% $MgSO_4 \cdot 7H_2O$, and 0.06% $CaCl_2$.

Controls A and B were run by the same procedure as Examples 1–4 in order to show the effect of employing each monomer without the other. The results provide a comparative basis for establishing synergism of the monomer combinations.

The results are shown in Table I.

EXAMPLE 5

A heavy dough was prepared from $AASO_3H$, acrylamide, water, and pregelatinized wheat starch as described in Example 3. The bottle containing the reaction mass was cooled in ice water for 50 minutes and was then evacuated to 50 mm. and repressured with nitrogen four times. The bottle was packed in ice water, irradiated with Cobalt-60 to a total dose of 0.5 Mrad, and finally removed from the ice bath and let stand at ambient temperature for 2 hours. Work-up as in Example 3 yielded a graft copolymer with 50% add-on and a water absorbency of 272 g./g.

EXAMPLES 6–7

The procedure was the same as for Examples 1–4 with the exception that a total dose of 0.1 Mrad of Cobalt-60 was used. Control C illustrates the result of having less than 25% add-on. The results are shown in Table II.

Table I

| Example | Acrylamide, g. | AASO$_3$H, g. | Starch, g. | % Add-on | Water absorbency, g./g. | Synthetic urine absorbency, g./g. |
|---|---|---|---|---|---|---|
| Control A | 10 | 0 | 10 | 50 | 12 | |
| 1 | 9 | 1 | 10 | 50 | 160 | 13 |
| 2 | 7.5 | 2.5 | 10 | 50 | 540 | 28 |
| 3 | 5 | 5 | 10 | 50 | 750 | 26 |
| 4 | 2.5 | 7.5 | 10 | 50 | 1,200 | 26 |
| Control B | 0 | 10 | 10 | 50 | disperses | |

Table II

| Example | Acrylamide, g. | AASO$_3$H, g. | Starch, g. | % Add-on | Water absorbency, g./g. |
|---|---|---|---|---|---|
| 6 | 5 | 5 | 10 | 50 | 2,130 |
| 7 | 2 | 2 | 10 | 29 | 710 |
| Control C | 1 | 1 | 10 | 17 | 80 |

EXAMPLE 8

Example 5 was repeated with the exception that a total dose of 0.1 Mrad of Cobalt-60 irradiation was used. The resulting graft copolymer had a 50% add-on and a water absorbency of 800 g./g.

EXAMPLE 9

A. A solution of 2 g. of acrylamide and 2 g. of $AASO_3H$ in 4 ml. of water was prepared in a 2-oz. screw cap bottle. Granular unmodified corn starch (10 g., dry basis; water content, 13%) was added and the mixture blended with a spatula to give a heavy paste. Oxygen was removed by evacuating to 50 mm. and repressuring with nitrogen (four times). The bottle was capped, irradiated with Cobalt-60 to a total dose of 0.1 Mrad, and then let stand at ambient temperature for 2 hours. The resulting graft copolymer, isolated as in Examples 1–4, had a 28% add-on and had a water absorbency of 9 g./g.

B. One gram of the graft copolymer was dispersed in 100 ml. of water at room temperature and then titrated with dilute sodium hydroxide solution to a pH of 7.0. The dispersion was heated to 95° C., poured onto a "Teflon"-coated tray, and dried in a forced air oven near room temperature. The resulting film had a water absorbency of 228 g./g.

EXAMPLE 10

The procedure of Example 3 was repeated with the exception that 2-sulfoethyl methacrylate (2-SEM) was used instead of $AASO_3H$. The resulting graft copolymer had a 50% add-on and had a water absorbency of 120 g./g.

EXAMPLES 11–12

A stirred dispersion of 10 g. (dry basis) of unmodified corn starch (moisture content, 12%) in 167 ml. of water was sparged with a slow stream of nitrogen, heated to 85° C., held at 85° C. for 30 minutes until the starch was gelatinized, and finally cooled back to 25° C. Acrylonitrile and $AASO_3H$ were added followed after 5 minutes by a solution of 0.338 g. of ceric ammonium nitrate in 3 ml. of 1 N nitric acid. The mixture was allowed to stir under nitrogen at 25°–28° C. for at least 2 hours, to insure completeness of reaction, and was then diluted with 200 ml. of acetone. The graft copolymer was separated by centrifugation, extracted with isopropanol to remove any unreacted monomer, and allowed to air dry. Percent add-on was calculated from the gain in weight of starch due to graft polymerization, and water absorbency was determined as in Examples 1–4.

Controls D and E were run by the same procedure as Examples 11 and 12 in order to show the effect of operating outside of suitable proportions for the AN-$AASO_3H$ system.

The results are shown in Table III.

EXAMPLE 13

A 0.1-g. sample of the graft copolymer of Example 12 was added to 20 ml. of distilled water. The pH of the resulting gel was 2.8.

Distilled water was adjusted to pH 3.2 by the addition of hydrochloric acid. The graft copolymer of Example 12 absorbed 230 times its weight of this acidified water.

EXAMPLE 14

A stirred dispersion of 10 g. (dry basis) of granular unmodified corn starch (moisture content, 12%) in 167 ml. of water was sparged with a slow stream of nitrogen at 25° C. for 40 minutes. Acrylonitrile (7.5 g.) and 12.5 g. of AASO$_3$H were added followed after 5 minutes by a solution of 0.338 g. of ceric ammonium nitrate in 3 ml. of 1 N nitric acid. The mixture was allowed to stir under nitrogen at 25°–28° C. for 2 hours, and the graft copolymer was isolated as in Examples 11 and 12. The graft copolymer had a 41% add-on and a water absorbency of 320 g./g.

EXAMPLE 15

A solution of 6.25 g. of AASO$_3$H in 10 ml. of water was prepared in a 2-oz. screw cap bottle. Acrylonitrile (3.85 g.) was added followed by 10 g. (dry basis) of pregelatinized wheat starch. The mixture was blended with a spatula to give a heavy dough, cooled in ice water for about 1 hour, and the oxygen removed by evacuating to 100 mm. and repressuring with nitrogen (four times). The bottle was packed in ice water and irradiated with Cobalt-60 to a total dose of Table III

| Example | Acrylonitrile, g. | AASO$_3$H, g. | Starch, g. | % Add-on | Water absorbency, g./g. |
|---|---|---|---|---|---|
| Control D | 12.5 | 7.5 | 10 | 54 | 20 |
| 11 | 10 | 10 | 10 | 54 | 220 |
| 12 | 7.5 | 12.5 | 10 | 54 | 650 |
| Control E | 5 | 15 | 10 | 6 | — |

0.25 Mrad. The reaction mixture was allowed to stand at ambient temperature for 2 hours, and the graft copolymer was then isolated as in Examples 1–4. The graft copolymer had a 44% add-on and a water absorbency of 175 g./g.

EXAMPLE 16

A solution of 6.25 g. of AASO$_3$H in 10 ml. of water was prepared in a 2-oz. screw cap bottle, and 3.75 g. of methyl methacrylate was then added. Ten grams (dry basis) of pregelatinized wheat starch was added and the mixture blended with a spatula to give a heavy dough. The mixture was cooled in ice wter for 30 minutes and was then evacuated to 50 mm. and repressured with nitrogen four times. The bottle was capped, irradiated with Cobalt-60 to a total dose of 0.25 Mrad, and allowed to stand for 2 hours at ambient temperature. Work-up as in Examples 1–4 yielded a graft copolymer with 32% add-on and a water absorbency of 168 g./g.

EXAMPLE 17

The procedure of Example 16 was repeated with the exception that methyl acrylate was substituted for methyl methacrylate. The resulting graft copolymer had 33% add-on and a water absorbency of 223 g./g.

It is understood that the foregoing detailed description is given merely by way of illustration and that modification and variations may be made therein without departing from the spirit and scope of the invention.

We claim:

1. A method of preparing water-insoluble, aqueous fluid-absorbing compositions without saponification comprising the following steps:
   a. graft polymerizing a nonionic acrylic monomer and an anionic sulfonic acid-substituted acrylic monomer onto a starch substrate, thereby forming an unsaponified water-insoluble graft copolymer, wherein the copolymerized nonionic monomer and anionic monomer comprise a synthetic copolymer moiety of said graft copolymer, and the weight ratio of nonionic monomer:anionic monomer in said synthetic copolymer moiety is in the range of about 9:1 to about 1:4, and wherein the weight ratio of starch:synthetic copolymer moiety is in the range of 3:1 to 1:3;
   b. drying said unsaponified water-insoluble graft copolymer from step (a) to a moisture level in the range of about 1 to 15% water by dry weight; and
   c. recovering said unsaponified graft copolymer from step (b).

2. The method as described in claim 1 wherein the nonionic acrylic monomer is selected from the group consisting of acrylamide, acrylonitrile, methyl acrylate, and methyl methacrylate.

3. The method as described in claim 1 wherein the anionic sulfonic acid-substituted acrylic monomer is 2-acrylamido-2-methylpropane sulfonic acid.

4. The method as described in claim 1 wherein the anionic sulfonic acid-substituted acrylic monomer is 2-sulfoethyl methacrylate.

5. The method as described in claim 1 wherein said starch substrate is granular starch.

6. The method as described in claim 1 wherein said starch substrate is gelatinized starch.

7. The method as described in claim 1 wherein said starch substrate is gelatinized starch, said nonionic monomer is acrylamide, and said anionic monomer is 2-acrylamido-2-methylpropane sulfonic acid, and wherein the weight ratio of nonionic monomer:anionic monomer is in the range of about 3:1 to about 1:3 and the weight ratio of starch:synthetic copolymer moiety is about 1:1.

8. The method as described in claim 1 wherein said starch substrate is gelatinized starch, said nonionic monomer is acrylonitrile, and said anionic monomer is 2-acrylamido-2-methylpropane sulfonic acid, and wherein the weight ratio of nonionic monomer:anionic monomer is in the range of about 1:1 to about 3:5 and the weight ratio of starch:synthetic copolymer moiety is in the range of about 1:1 to about 1:2.

9. An aqueous fluid-absorbing composition comprising a water-insoluble unsaponified graft copolymer of a starch substrate, a nonionic acrylic monomer, and an anionic sulfonic acid-substituted acrylic monomer, wherein the copolymerized nonionic monomer and anionic monomer comprise a synthetic copolymer moiety of said graft copolymer, and the weight ratio of nonionic monomer:anionic monomer in said synthetic copolymer moiety is in the range of about 9:1 to about 1:4, and wherein the weight ratio of starch:synthetic copolymer moiety is in the range of 3:1 to 1:3.

10. The aqueous fluid-absorbing composition as described in claim 9 wherein the nonionic acrylic monomer is selected from the group consisting of acrylamide, acrylonitrile, methyl acrylate, and methyl methacrylate.

11. The aqueous fluid-absorbing composition as described in claim 9 wherein the anionic sulfonic acid-substituted acrylic monomer is 2-acrylamido-2-methylpropane sulfonic acid.

12. The aqueous fluid-absorbing composition as described in claim 9 wherein the anionic sulfonic acid-substituted acrylic monomer is 2-sulfoethyl methacrylate.

13. The aqueous fluid-absorbing composition as described in claim 9 wherein said starch substrate is granular starch.

14. The aqueous fluid-absorbing composition as described in claim 9 wherein said starch substrate is gelatinized starch.

15. The aqueous fluid-absorbing composition as described in claim 9 wherein said starch substrate is gelatinized starch, said nonionic monomer is acrylamide, and said anionic monomer is 2-acrylamido-2-methylpropane sulfonic acid, and wherein the weight ratio of nonionic monomer:anionic monomer is in the range of about 3:1 to about 1:3 and the weight ratio of starch:synthetic copolymer moiety is about 1:1.

16. The aqueous fluid-absorbing composition as described in claim 9 wherein said starch substrate is gelatinized starch, said nonionic monomer is acrylonitrile, and said anionic monomer is 2-acrylamido-2-methylpropane sulfonic acid, and wherein the weight ratio of nonionic monomer:anionic monomer is in the range of about 1:1 to about 3:5, and the weight ratio of starch:-synthetic copolymer moiety is in the range of about 1:1 to about 1:2.

* * * * *